United States Patent [19]
Hubert-Habart et al.

[11] Patent Number: 5,828,437
[45] Date of Patent: Oct. 27, 1998

[54] EYE PROTECTION DEVICE

[75] Inventors: Christophe Hubert-Habart, Meudon; Michel Jean Lavergne, Marselle, both of France

[73] Assignees: Aerospatiale Societe Nationale Industrielle, Paris; Eurocopter France, Marignane Cedex, both of France

[21] Appl. No.: 769,006

[22] Filed: Dec. 18, 1996

[30] Foreign Application Priority Data

Dec. 18, 1995 [FR] France .................................. 95 14961

[51] Int. Cl.$^6$ .............................. G02C 7/10; G02B 27/02
[52] U.S. Cl. ................................ 351/44; 351/45; 359/480
[58] Field of Search ............................... 351/44, 45, 158; 359/1, 902, 480, 481, 482, 227, 229, 237, 241; 2/432

[56] References Cited

U.S. PATENT DOCUMENTS

| | | | |
|---|---|---|---|
| 3,519,339 | 7/1970 | Hutchinson et al. | 351/44 |
| 4,835,796 | 6/1989 | Wiedner | 351/44 |
| 4,909,609 | 3/1990 | McDowell | 359/241 |
| 4,978,208 | 12/1990 | Hsu et al. | 351/45 |
| 5,377,037 | 12/1994 | Branz et al. | 351/45 |

FOREIGN PATENT DOCUMENTS

| | | |
|---|---|---|
| 0436845 | 7/1991 | European Pat. Off. . |
| 2553005 | 6/1977 | Germany . |
| 3313899 | 10/1984 | Germany . |

*Primary Examiner*—Huy Mai
*Attorney, Agent, or Firm*—Fisher, Christen & Sabol

[57] ABSTRACT

A device placed by a support in front of the eyes of a user protects them against luminous aggression, in particular by a laser beam. The device includes a light attenuation system to attenuate the intensity of the received beam by a particular attenuation value. A light amplification system is disposed between the light attenuation system and the eyes of the user to amplify the intensity of the light received from the light attenuation system by a particular amplification value, but such that the intensity of the light transmitted towards the eyes does not exceed a prescribed maximal intensity that is not harmful for the eyes. The attenuation and amplification values are substantially equal.

17 Claims, 3 Drawing Sheets

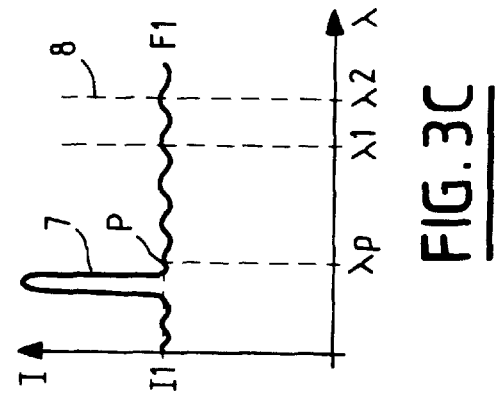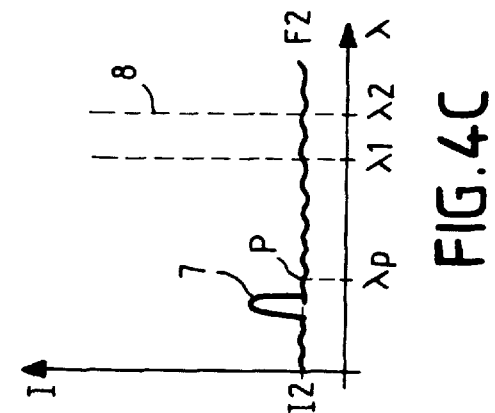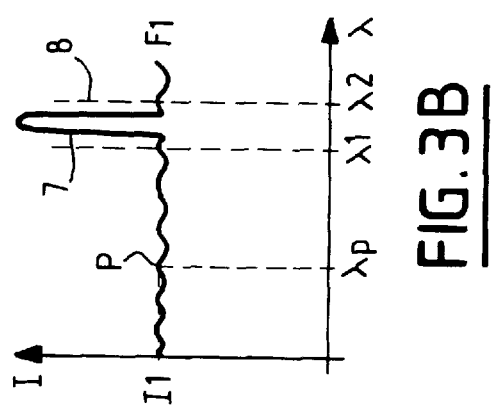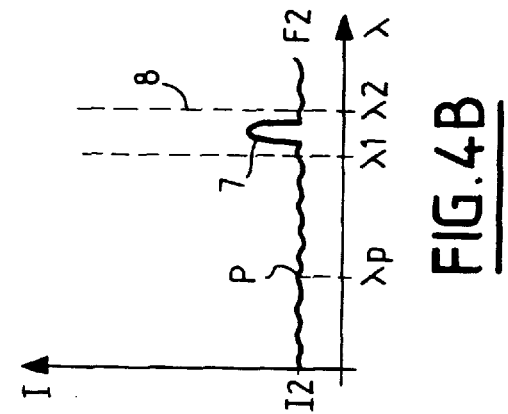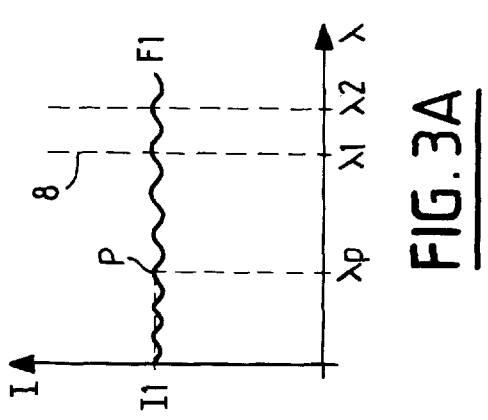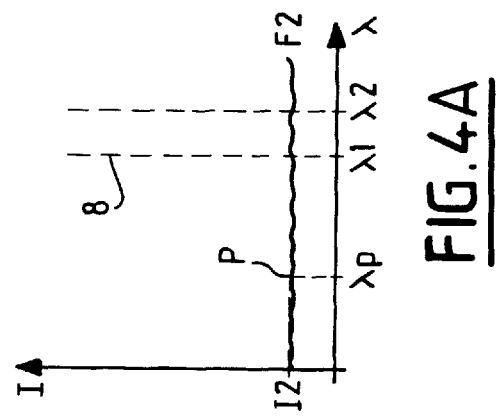

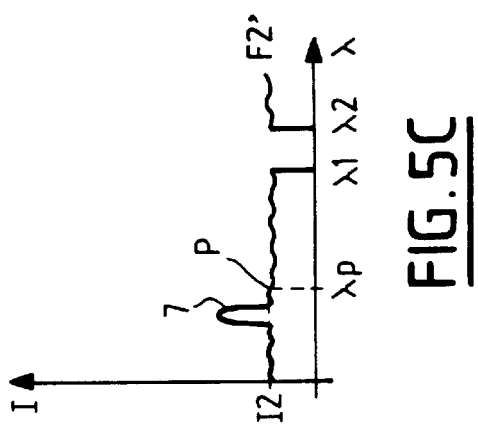
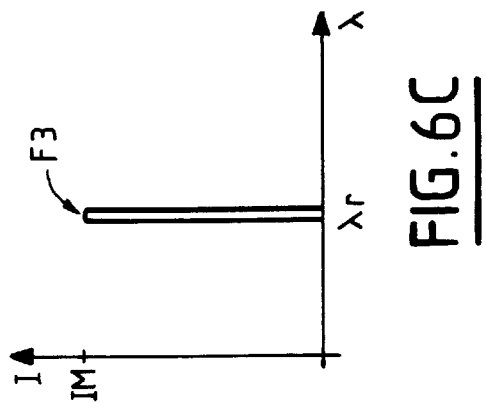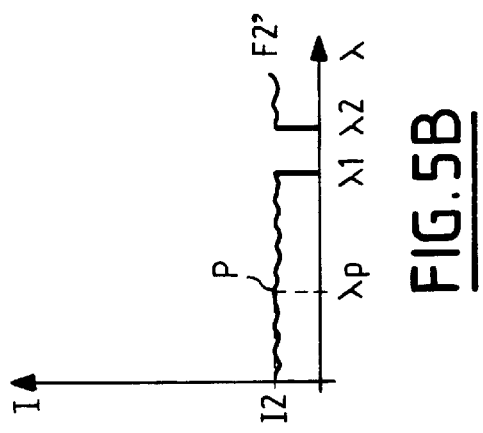
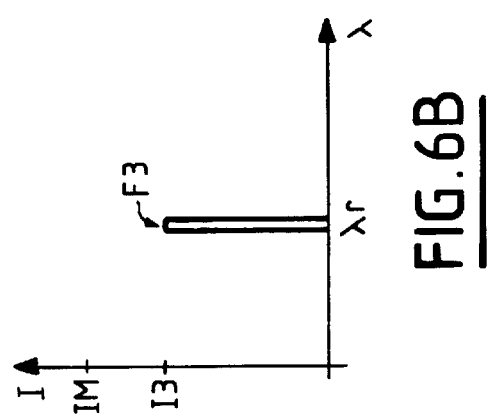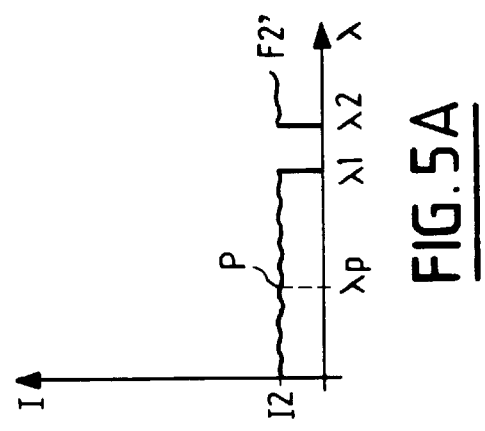
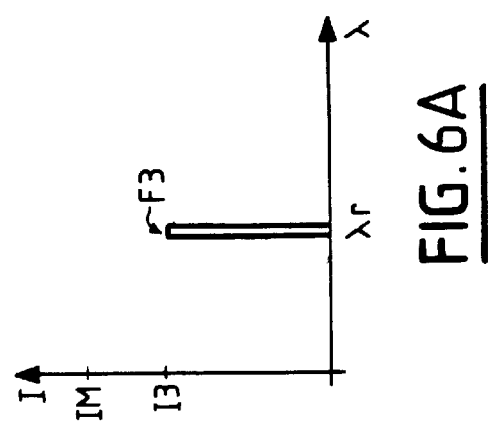

EYE PROTECTION DEVICE

BACKGROUND OF THE INVENTION

1. Field of the Invention

The present invention concerns a device for protecting the eyes of a user against luminous aggression, in particular from a laser beam.

Although not exclusively, the present invention applies more particularly to protection against low-power and medium-power laser weapon systems that are susceptible, when used against persons, to dazzle or blind or to cause even ocular lesions.

Such luminous aggression can have irreversible consequences, in particular when the persons targeted are drivers of vehicles, notably pilots of airborne vehicles, such as helicopter pilots, for example.

2. Description of the Prior Art

Various means of protection against luminous aggression are known in themselves, mounted either on the goggles or visors of the pilot or on the windshield of the vehicle.

They include passive filter type protection means and active protection means with selectively operable shutters.

Passive protection means using filters, for example colored filters or band-stop filters, provide effective protection only against laser beams that have a clearly defined and known wavelength. They are ineffective against luminous aggression by lasers with more than one wavelength or variable wavelengths.

Colored filters, which are wavelength-selective in terms of their absorbency, are characterized by a wide absorption peak and are therefore strongly colored, especially if the wavelength to be protected against is in the visible light band, and this disturbs the color sense of the user of the protection. This defect, associated with significant darkening when the protection covers a wide range of wavelengths in the visible spectrum, prevents them being used as such (in particular by helicopter pilots).

Protection by band-stop filters, namely multidielectric and/or holographic interference filters, is limited to a few (between 3 and 7) protection wavelengths since, for a greater number, the photopic or scotopic transmission factor of the filter becomes too low for comfortable vision to be obtained.

Active protection means, such as electro-optical masks, activated after detection of an aggressive laser beam by one or more sensors have a response time that is too long (greater than 0.1 microsecond) to be effective against laser beams (the triggering time of which can be less than around 10 nanoseconds).

SUMMARY OF THE INVENTION

An object of the present invention is to remedy these drawbacks. It concerns a device adapted to be placed by means of a support in front of the eyes of a user and effectively protecting the eyes of said user against any luminous aggression, regardless of its wavelength, and in particular against luminous aggression by a laser beam.

To this end, in accordance with the invention, said device is noteworthy in that it comprises:

a light attenuation system adapted to attenuate the intensity of the received beam by a particular attenuation value; and a light amplification system disposed between said light attenuation system and the eyes of the user and adapted to amplify the intensity of the light received from said light attenuation system by a particular amplification value, but such that the intensity of the light transmitted towards the eyes does not exceed a prescribed maximal intensity that is not harmful for the eyes, said attenuation and amplification values being substantially equal.

Thus, by virtue of the invention, the eyes of a user are effectively protected since the intensity of the light transmitted by the device of the invention is such that it cannot harm the eyes. It cannot dazzle or blind or cause ocular lesions.

As the attenuation and amplification values are substantially equal, the intensity of the light picked up by the eyes is close to that of the background illumination of the environment (possibly reduced by certain intensities that are too high).

Consequently, the device of the invention eliminates from the incident luminous spectrum high luminous intensities likely to be harmful.

Note that in the context of the present invention said light attenuation and amplification systems are of course provided with all means necessary to their operation, and in particular with electrical current power supply means, and this applies regardless of the embodiment concerned.

Advantageously, said light attenuation system includes:

a wideband linear attenuation light filter; and/or a fixed diaphragm; and/or a variable diaphragm, for example of the mechanical or liquid crystal type.

Of course, the opening of said variable diaphragm may be commanded manually. However, in one advantageous embodiment of the invention this opening is commanded automatically as a function of the mean level of illumination sensed by a photo-electric cell.

The device of the invention advantageously includes an optical protection system adapted to protect said device against luminous radiation at a particular wavelength.

In accordance with the invention, said optical protection system advantageously includes:

at least one band-stop filter for eliminating a band of wavelengths including the wavelength or wavelengths of one or more known lasers adapted to be used as weapons; or at least one band-pass, for example colored, interferometric or holographic, filter transmitting only bands of wavelengths in which lasers usable for military purposes do not have their main emission wavelengths.

If the device of the invention is a binocular device, the optical protection system preferably includes two band-pass filters with different pass bands, each of said band-pass filters being associated with one eye of the user and being adapted to protect the part of the light attenuation system and of the light amplification system placed in front of the corresponding eye, which increases the probability of at least partial protection of the device of the invention since a laser beam that is not eliminated by the first of said filters and could destroy the part of the device protected by the first filter can be eliminated by the second filter so that the part of the device protected by the second filter is not destroyed.

In one particular advantageous embodiment of the invention, said light attenuation system and said light amplification system form a single and homogeneous optical system, enabling the device of the invention to be made as a robust and compact single unit.

Note that, in another embodiment of the invention, said support and said light amplification system can form night vision binoculars, i.e. a commercially available device, with which the optical protection system and the light attenuation system are associated to obtain the device of the invention. Said optical protection system and said light attenuation system are advantageously retractable so as to preserve intact the operating characteristics at night of the night vision binoculars.

However, this other embodiment has the disadvantage that the light attenuation system must be formed in such a manner as to provide in daylight illumination conditions identical to those at night to enable the use of said night vision binoculars, which is not the case in the previous embodiment in which the only requirement is for the attenuation and amplification values to be substantially equal.

Moreover, this latter embodiment of the device is generally relatively large in overall size and relatively heavy.

The figures of the accompanying drawings explain how the invention may be put into effect. In the figures, identical reference numbers designate similar components.

BRIEF DESCRIPTION OF THE DRAWINGS

FIGS. 3A, 3B and 3C show the luminous intensity of three different incident light beams selected to explain the operation of the device of the invention.

FIGS. 4A through 4C, 5A through 5C and 6A through 6C show respective successive modifications of the intensity of the incident light beams from FIGS. 3A through 3C on passing through the optical system from FIG. 2.

DETAILED DESCRIPTION OF THE PREFERRED EMBODIMENT

Figure 1:
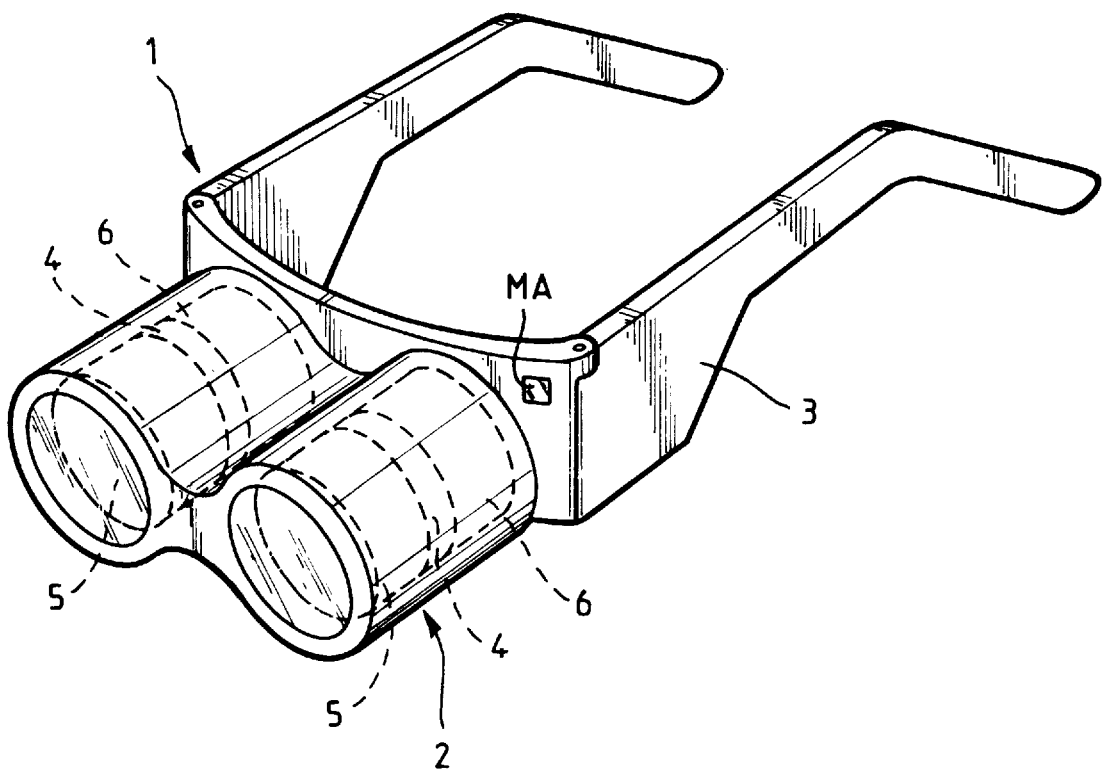
FIG. 1 is a partly diagrammatic perspective view of a device of the invention.

The device 1 of the invention shown in FIG. 1 includes an optical system 2 mounted on a support 3 of the eyeglass frame type and is adapted to protect the eyes O of a user, not shown, against luminous aggression, in particular from a laser beam.

Although not exclusively, the device 1 is more particularly intended to protect the eyes of persons, for example the drivers of terrestrial vehicles or the pilots of airborne vehicles, such as helicopter pilots, likely to be illuminated by low-power or medium-power laser weapon systems that can dazzle and blind and even cause ocular lesions and are consequently liable to be extremely harmful.

For this type of application the support 3 may be attachable directly to the head or to the helmet of the pilot, so that the device 1 is held in position even under unfavorable environmental conditions, for example vibration or acceleration.

Figure 2:
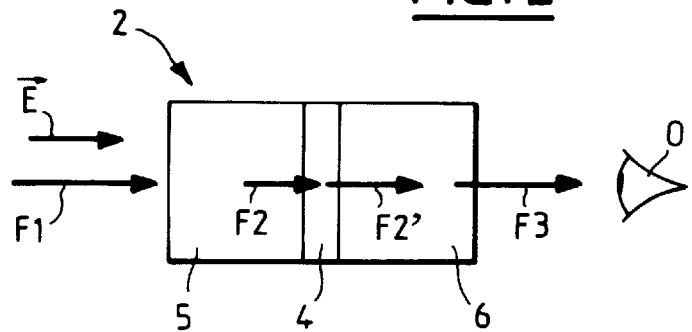
FIG. 2 is a diagram showing the optical system of a device of the invention.

In accordance with the invention, to protect the eyes O of a user against luminous aggression, said optical system 2 shown diagrammatically in FIG. 2 includes, successively in the direction $\vec{E}$ of travel of the light towards the eye O:

a light attenuation system 5 adapted to attenuate by a particular value the intensity I of the received incident light F1 so as to transmit a light F2;

optionally, an optical protection system 4 protecting the system 2 against high power light beams at particular wavelengths; and a light amplification system 6 adapted to amplify the intensity I of the light F2' received from said light attenuation system 5 and from said optical protection system 4, if present, by a particular value, but such that the intensity I of the light F3 transmitted towards the eyes O does not exceed a prescribed maximal intensity IM that is not harmful to the eyes O, said attenuation and amplification values being substantially equal.

Accordingly, in accordance with the invention, the intensity I of the light beam F3 reaching the eye does not exceed the value IM, regardless of the frequency components and the intensity of the incident light beam F1, with the result that the eyes O are effectively protected.

Note that in one particular embodiment, not shown, said optical protection system may be mounted on the upstream (in the direction in which the light travels towards the eye) side of the light attenuation system.

The device 1 of the invention also includes electrical current power supply means MA, of a type known in itself, shown diagrammatically in FIG. 1 and connected in a manner that is not shown to the components of the device 1 requiring an electrical current power supply.

FIGS. 3A through 3C, 4A through 4C, 5A through 5C and 6A through 6C show the successive modifications of the intensity of three different light beams F1 on passing through the optical system 2 in the direction $\vec{E}$. In these figures, the letters A, B and C correspond to the three different cases considered by way of example and specified hereinafter and the digits 3 through 6 indicate the various successive modifications for each of the latter.

It is assumed that the incident beam F1 reaching the device 1 has a luminous intensity as a function of the wavelength λ like that shown in the diagram of FIGS. 3A, 3B and 3C, respectively, for the three cases envisaged.

In cases "B" and "C", the incident beam F1 has a high intensity peak 7, coming from a laser source or some other light source, for example, and likely to dazzle or to injure the eyes O of a person.

On said FIGS. 3A, 3B and 3C there is also shown a luminous background point P of intensity I1 corresponding to the intensity of the incident beam F1 at a wavelength λp.

This intensity of said incident beam F1 is attenuated by the light attenuation system 5 by a particular attenuation value that is identical throughout the range of wavelengths considered, to obtain at the output of said light attenuation system 5 the beam F2 shown in FIGS. 4A through 4C, respectively, for the three cases envisaged.

Because of this attenuation, the point P represents an intensity I2 corresponding to the ratio between the intensity I1 (FIGS. 3A through 3C) and the chosen attenuation value.

In accordance with the invention, said light attenuation system 5 includes at least one of the following components:
 a wideband linear attenuation filter;
 a fixed diaphragm;
 a mechanical or liquid crystal variable diaphragm adapted to be commanded manually or automatically according to the mean level of illumination sensed by a photoelectric cell, not shown.

Said beam F2 is then modified into a beam F2', as shown in FIGS. 5A through 5C, by the optical protection system 4 that is adapted to protect the optical system 2 against certain high power laser beams that could destroy said optical system 2 by eliminating certain bands of wavelengths including the wavelengths of known lasers that can be used by a possible enemy, for example a band 8 between the wavelength λ1 and λ2 and shown diagramatically by way of example in FIGS. 3A through 3C and 4A through 4C.

To eliminate this band 8 the optical protection system 4 includes a band-stop filter covering the appropriate wavelength.

As seen particularly in FIGS. 4B and 4C, in the case "B" the intensity peak 7 is in said band 8 and in case "C" said intensity peak 7 is outside said band 8.

Of course, said optical protection system 4 may include other types of filters, for example passband filters of the colored, interferometric or holographic type, that pass towards the light amplification system 6 only certain bands of wavelengths in which lasers usable for military purposes do not have their main emission wavelength.

Finally, the light amplification system 6 amplifies the intensity I of said beam F2' by a particular amplification value so as to transmit to the eye O the beam F3 shown in FIGS. 6A through 6C, respectively, according to the case envisaged. Said beam F3 corresponds to the beam from a monochrome light amplification system with an output wavelength λr.

The amplification effected by the system 6 has two features:

firstly, the amplification value used is substantially equal to the attenuation value of the system 5, allowing if necessary for any attenuation of luminous intensity by the optical protection system 4, so as to obtain an intensity I3 substantially equal to that of the incident beam F1;

secondly, the intensity I of the transmitted beam F3 does not exceed the prescribed maximal intensity IM. Consequently, all the high intensity peaks like the peak 7 that can be harmful to and injure the eye are reduced to an intensity equal at most to the intensity IM.

Accordingly, by virtue of the invention, the eye O receives said light beam F3 that has an intensity globally similar to that of the incident beam F1 but that does not include either any high intensity peaks that may be harmful to the eye or wavelengths outside the output band.

In the preferred embodiment shown in FIGS. 1 and 2, the device 1 is based on an optical system 2 forming a single and homogeneous unit, providing a device 1 that is compact and small in overall size.

In a different embodiment, not shown, the support 3 and the light amplification system 6 can be a commercially available device, namely night vision binoculars, with which the optical protection system 4 and the light attenuation system 5 are associated to obtain the device of the invention.

However, this embodiment has the disadvantage that the light attenuation system 5 must be formed in such a manner as to create illumination conditions in daylight identical to those existing at night in order to enable the use of said night vision binoculars, which imposes very strict implementation conditions on said light attenuation system 5, unlike the device 1 as previously described.

Moreover, the device is then bulky and lacking in homogeneity because of the arrangement of external components on existing equipment (i.e. the night vision binoculars).

There is claimed:

1. Device adapted to be placed by means of a support in front of the eyes of a user to protect the eyes against luminous aggression, in particular by a laser beam, including:

a light attenuation system adapted to attenuate the intensity of the received beam by a particular attenuation value; and a light amplification system disposed between said light attenuation system and said eyes of said user and adapted to amplify the intensity of the light received from said light attenuation system by a particular amplification value, wherein the intensity of the light transmitted towards said eyes does not exceed a prescribed maximal intensity that is not harmful for said eyes, said attenuation and amplification values being substantially equal.

2. The device claimed in claim 1 wherein said light attenuation system includes a wideband linear attenuation filter.

3. The device claimed in claim 1 wherein said light attenuation system includes a fixed diaphragm.

4. The device claimed in claim 1 wherein said light attenuation system includes a variable diaphragm.

5. The device claimed in claim 4 wherein said variable diaphragm is a mechanical diaphragm.

6. The device claimed in claim 4 wherein said variable diaphragm is a liquid crystal diaphragm.

7. The device claimed in claim 4 wherein the aperture of said variable diaphragm is commanded automatically according to a mean illumination level sensed by a photo-electric cell.

8. A device as claimed in claim 1 including an optical protection system adapted to protect said device against luminous radiation at a particular wavelength.

9. The device claimed in claim 8 wherein said optical protection system includes at least one band-stop filter.

10. The device claimed in claim 8 wherein said optical protection system includes at least one band-pass filter.

11. The device claimed in claim 10 wherein said band-pass filter is a colored filter.

12. The device claimed in claim 10 wherein said band-pass filter is a interferometric filter.

13. The device claimed in claim 10 wherein said band-pass filter is a holographic filter.

14. The device claimed in claim 8, of binocular form, wherein said optical protection system includes two band-pass filters with different pass-bands, each of said band-pass filters being associated with one eye of said user and being adapted to protect the part of said light amplification system and where applicable said light attenuation system placed in front of the corresponding eye.

15. The device claimed in claim 1 wherein said light attenuation system and said light amplification system form a single optical system.

16. The device claimed in claim 1 wherein said support and said light amplification system constitute night vision binoculars.

17. The device claimed in claim 16 wherein said light attenuation system and said optical protection system are retractable.

* * * * *